United States Patent [19]

Tokura

[11] Patent Number: 5,598,345
[45] Date of Patent: Jan. 28, 1997

[54] METHOD AND APPARATUS FOR INSPECTING SOLDER PORTIONS

[75] Inventor: Nobufumi Tokura, Fukuoka-ken, Japan

[73] Assignee: Matsushita Electric Industrial Co., Ltd., Osaka, Japan

[21] Appl. No.: 225,944

[22] Filed: Apr. 11, 1994

Related U.S. Application Data

[63] Continuation-in-part of Ser. No. 795,151, Nov. 20, 1991, abandoned.

[30] Foreign Application Priority Data

Nov. 29, 1990 [JP] Japan ................................ 2-333924

[51] Int. Cl.[6] ..................................................... G06F 17/50
[52] U.S. Cl. ........................ 364/489; 364/488; 364/490; 382/145; 382/150; 382/156
[58] Field of Search ................................ 364/488–491, 364/552, 562; 356/237, 302, 357, 381, 392, 376; 382/146, 150, 141, 145, 147, 148, 149, 155, 156

[56] References Cited

U.S. PATENT DOCUMENTS

| | | | |
|---|---|---|---|
| 4,218,142 | 8/1980 | Kryger et al. | 356/394 |
| 4,422,764 | 12/1983 | Eastman | 356/357 |
| 4,454,585 | 6/1984 | Ele | 364/507 |
| 4,481,664 | 11/1984 | Linger et al. | 382/8 |
| 4,573,073 | 2/1986 | Corby, Jr. | 358/96 |
| 4,589,140 | 5/1986 | Bishop et al. | 382/8 |
| 4,646,253 | 2/1987 | Rehme et al. | 364/527 |
| 4,650,333 | 3/1987 | Crabb et al. | 356/367 |
| 4,677,473 | 6/1987 | Okamoto et al. | 358/101 |
| 4,809,308 | 2/1989 | Adams et al. | 378/99 |
| 4,851,902 | 7/1989 | Tezuka et al. | 358/101 |
| 4,852,131 | 7/1989 | Armistead | 378/4 |
| 4,866,629 | 9/1989 | Chen et al. | 364/468 |
| 4,893,346 | 1/1990 | Bishop | 382/8 |
| 4,894,790 | 1/1990 | Yotsuya et al. | 364/552 |
| 4,926,491 | 5/1990 | Maeda et al. | 382/14 |
| 4,957,369 | 9/1990 | Antonsson | 356/376 |
| 4,978,224 | 12/1990 | Kishimoto et al. | 356/394 |
| 4,999,785 | 3/1991 | Schmuter | 364/507 |
| 5,027,295 | 6/1991 | Yotsuya | 364/552 |

(List continued on next page.)

FOREIGN PATENT DOCUMENTS

| | | |
|---|---|---|
| 0355377A1 | 2/1990 | European Pat. Off. . |
| 0471196A2 | 2/1992 | European Pat. Off. . |
| 3838032 | 5/1989 | Germany . |
| 1-79874 | 3/1989 | Japan . |

OTHER PUBLICATIONS

Bartlett, S. L., et al. "Automatic Solder Joint Inspection," IEEE Trans on Pattern Analysis and Machine Intelligence, vol. 10, No. 1, Jan. 1988, pp. 31–43.

Besl, P. J., et al. "Automatic Visual Solder Joint Inspection," IEEE Journal of Robotics and Automation, vol. RA–1, No. 1, Mar. 1985, pp. 42–56.

(List continued on next page.)

*Primary Examiner*—Kevin J. Teska
*Assistant Examiner*—Leigh Marie Garbowski
*Attorney, Agent, or Firm*—Lowe, Price, LeBlanc & Becker

[57] ABSTRACT

An image taking device serves to take an image of an object to be inspected, and outputs an image signal representative thereof. A first deciding device serves to decide a condition of the object in response to the image signal. A measuring device serves to measure a shape of the object, and outputs a height signal representative of a height of the object. A second deciding device serves to decide a condition of the object in response to the height signal. A control device serves to, in cases where the first deciding device can not detect the condition of the object, enable the measuring device to measure the shape of the object and enable the second deciding device to decide the condition of the object, and enable the first deciding device to execute a leaning process on the object in response to a result of the decision by the second deciding device.

16 Claims, 10 Drawing Sheets

U.S. PATENT DOCUMENTS

| | | | |
|---|---|---|---|
| 5,046,113 | 9/1991 | Hoki | 382/8 |
| 5,058,178 | 10/1991 | Ray | 382/8 |
| 5,093,797 | 3/1992 | Yotsuya et al. | 364/489 |
| 5,103,105 | 4/1992 | Ikegaya et al. | 250/561 |
| 5,124,931 | 5/1992 | Iwamatsu et al. | 364/489 |
| 5,148,375 | 9/1992 | Horikami | 364/552 |
| 5,245,671 | 9/1993 | Kobayashi et al. | 382/8 |
| 5,293,324 | 3/1994 | Tokura | 364/552 |

OTHER PUBLICATIONS

Blanz, W. E., et al. "Image Analysis Methods for Solder--Ball Inspection in IC Manufacturing," IEEE Journal of Robotics and Automation, vol. 4, No. 2, Apr. 1988, pp. 129–139.

Capson, D. W., et al. "A Tiered–Color Illumination Approach for Machine Inspection of Solder Joints," IEEE Trans on Pattern Analysis and Machine Intelligence, vol. 10, No. 3, May 1988, pp. 387–393.

Driels, M. R., et al. "Automatic Defect Classification of Printed Wiring Board Solder Joints," IEEE Trans on Components, Hybrids, and Manufacturing Technology, vol. 13, No. 2, Jun. 1990, pp. 331–340.

Jagannathan, S., et al. "Visual Inspection of Soldered Joints By Using Neural Networks," 1991 IEEE Int'l Conference on Neural Networks (Singapore), pp. 7–12.

Mengel, P., "Automated Inspection of Solder Joints on PC Boards Bysupplementary Processing of 3D and Gray–Level Images," IECON '90: Industrial Electronics Society 16th Annual Conference, pp. 786–791.

Mital, D. P., et al. "A Rule–Based Inspection System for Printed Circuit Boards," TENCON '89: IEEE Region IO Conference on Computers and Communication, pp. 665–668.

Muraoka, T., et al. "Applications of Laser Systems in Post Solder Inspection Equipment," IECON '90: Industrial Electronics Society 16th Annual Conference, pp. 805–810.

Pierce et al., "Automated Inspection of Through Hole Solder Joints Utilizing X–Ray Imaging," IEEE AES Systems Magazine, Feb. 1994, pp. 28–32.

Nakagawa, Y., "Automatic Visual Inspection of Solder Joints on Printed Circuit Boards," Robot Vision, Azriel Rosenfeld, Editor, Proc. SPIE 336, 121–127 (1982).

Von Lehmen et al., "Factors Influencing Learning by Back Propagation," 1988 IEEE Int'l Conference on Neural Networks, pp. 1–335–1–341.

Christian Gremli, "Probleme Erkennen und Fehler Finden", Technische Rundschau Jun. 1990, pp. 46–53.

Mlynski et al, "Expertensystem plant Einsatz Von Prufautomaten", Elektronik 18, Sep. 1, 1989, pp. 96–100.

Christian–Erik Thony, "Technik, die <<Sehen>> Kann", Technische Rundschau Mar. 1990, pp. 14–17.

Horst Bunke, "Computersehen Wird Industriereif", Technische Rundschau 38/90, pp. 136–143.

METHOD AND APPARATUS FOR INSPECTING SOLDER PORTIONS

CROSS-REFERENCES TO RELATED APPLICATIONS

This is a continuation-in-part of U.S. patent application, Ser. No. 795,151, filed on Nov. 20, 1991, now abandoned.

BACKGROUND OF THE INVENTION

1. Field of the Invention

This invention relates to a method and an apparatus for inspecting various objects such as solder portions on a circuit board.

2. Description of the Prior Art

U.S. Pat. No. 5,103,105 discloses an apparatus for inspecting solder portions of a circuit board. In the apparatus of U.S. Pat. No. 5,103,105, a beam of light is applied to a surface of a circuit board provided with at least one solder portion. The light beam scans the surface of the circuit board. Height data are derived from a portion of the light beam which is scattered at the surface of the circuit board. The height data represents a height of a currently-scanned point of the surface of the circuit board. The height data are accumulatively added for the solder portion. A variation in the height data is calculated. The accumulative addition of the height data is executed and suspended in response to the calculated variation in the height data. A decision is made as to whether the solder portion is acceptable or unacceptable on the basis of a result of the accumulative addition.

U.S. Pat. No. 4,650,333 discloses a non-contact system for detecting printed circuit wiring defects and for measuring circuit feature height relative to a substrate. The system has an energy source for illuminating the substrate and circuit features and a scanner for both instantaneously receiving energy reflected from the substrate and circuit features and for generating a signal in response to the reflected energy, which signal is adapted to vary with the intensity of the reflected energy. An analyzer is connected to the scanner for correlating the generated signal to a measurement representative of the height of the circuit features relative to the substrate. Variations and non-uniformity of the substrate surface due to bending, warpage or other causes can be accounted for so as to provide an accurate measurement of the height of a circuit feature relative to the substrate surface on which it is mounted.

According to U.S. Pat. No. 4,957,369, automatic acquisition and analysis for three-dimensional surface geometries is accomplished by use of an opto-electronic technique which exploits large-linear-area lateral-photo-effect-diodes and employs a reflected, tightly focused light spot. The technique consists of one very small light spot pulsed for example at 10,000 Hertz with a 50% duty cycle. The light spot is focused on the surface to be measured and scanned. The diode detectors, mounted in the focal plane of a pair of cameras, return azimuth and elevation information for each spot. Knowledge of the location and orientation of the cameras, as well as calibration corrections for each camera, completes the information necessary to reconstruct the full three-dimensional location of each reflected light spot.

SUMMARY OF THE INVENTION

It is an object of this invention to provide an improved method of inspecting, for example, a solder portion on a circuit board.

It is another object of this invention to provide an improved apparatus for inspecting, for example, a solder portion on a circuit board.

A first aspect of this invention provides an apparatus comprising image taking means for taking an image of an object to be inspected, and outputting an image signal representative thereof; first deciding means for deciding a condition of the object in response to the image signal; measuring means for measuring a shape of the object, and outputting a height signal representative of a height of the object; second deciding means for deciding a condition of the object in response to the height signal; and control means for, in cases where the first deciding means can not detect the condition of the object, enabling the measuring means to measure the shape of the object and enabling the second deciding means to decide the condition of the object, and enabling the first deciding means to execute a learning process on the object in response to a result of the decision by the second deciding means.

A second aspect of this invention provides a method comprising the steps of taking an image of an object to be inspected; first deciding a condition of the object in response to the image; measuring a shape of the object to derive height information representing a height of the object in cases where a result of the decision by the first deciding step is gray; and second deciding a condition of the object in response to the height information; wherein the first deciding step comprises executing a learning process on the object in response to a result of the decision by the second deciding step.

A third aspect of this invention provides an apparatus for inspecting a solder portion which comprises first means for detecting whether or not an image of a solder portion to be inspected is similar to one of images of typical solder portions to decide whether the inspected solder portion is acceptable or unacceptable; second means connected to the first means for detecting whether the inspected solder portion is acceptable or unacceptable to complement the decision by the first means when the first means detects the image of the inspected solder portion to be not similar to one of the images of the typical solder portions; and third means connected to the first means for, when the first means detects the image of the inspected solder portion to be not similar to one of the images of the typical solder portions, enabling the first means to learn the image of the inspected solder portion and adding the learned image of the inspected solder portion as an image of a new typical solder portion.

A fourth aspect of this invention provides an apparatus for inspecting a solder portion which comprises first means for detecting whether or not an image of a solder portion to be inspected is similar to one of images of typical solder portions each corresponding to either an acceptable solder portion or an unacceptable solder portion; second means connected to the first means for deciding the inspected solder portion to be acceptable when the first means detects the image of the inspected solder portion to be similar to one of images of typical solder portions each corresponding to an acceptable solder portion, and for deciding the inspected solder portion to be unacceptable when the first means detects the image of the inspected solder portion to be similar to one of images of typical solder portions each corresponding to an unacceptable solder portion; third means connected to the first means for detecting whether the inspected solder portion is acceptable or unacceptable when the first means detects the image of the inspected solder portion to be not similar to one of the images of the typical solder portions; and fourth means connected to the first means and the third means for enabling the first means to learn the image of the inspected solder portion, for adding the learned image of the inspected solder portion as an image of a new typical solder portion, and for providing a correspondence relation between the new typical solder portion and one of an acceptable solder portion and an unacceptable solder portion in response to a result of the detection by the third means in cases where the first means detects the image of the inspected solder portion to be not similar to one of the images of the typical solder portions.

A fifth aspect of this invention provides a method of inspecting a solder portion which comprises the steps of first detecting whether or not an image of a solder portion to be inspected is similar to one of images of typical solder portions to decide whether the inspected solder portion is acceptable or unacceptable; second detecting whether the inspected solder portion is acceptable or unacceptable to complement the decision by the first detecting step when the image of the inspected solder portion is detected to be not similar to one of the images of the typical solder portions by the first detecting step; and learning the image of the inspected solder portion and adding the learned image of the inspected solder portion as an image of a new typical solder portion in the detection by the first detecting step when the image of the inspected solder portion is detected to be not similar to one of the images of the typical solder portions by the first detecting step.

A sixth aspect of this invention provides a method of inspecting a solder portion which comprises the steps of first detecting whether or not an image of a solder portion to be inspected is similar to one of images of typical solder portions each corresponding to either an acceptable solder portion or an unacceptable solder portion; first deciding the inspected solder portion to be acceptable when the first detecting step detects the image of the inspected solder portion to be similar to one of images of typical solder portions each corresponding to an acceptable solder portion, and deciding the inspected solder portion to be unacceptable when the first detecting step detects the image of the inspected solder portion to be similar to one of images of typical solder portions each corresponding to an unacceptable solder portion; second detecting whether the inspected solder portion is acceptable or unacceptable when the first detecting step detects the image of the inspected solder portion to be not similar to one of the images of the typical solder portions; and learning the image of the inspected solder portion, adding the learned image of the inspected solder portion as an image of a new typical solder portion, and providing a correspondence relation between the new typical solder portion and one of an acceptable solder portion and an unacceptable solder portion in response to a result of the detection by the second detecting step in cases where the first detecting step detects the image of the inspected solder portion to be not similar to one of the images of the typical solder portions.

DESCRIPTION OF THE PREFERRED EMBODIMENT

Figure 1:
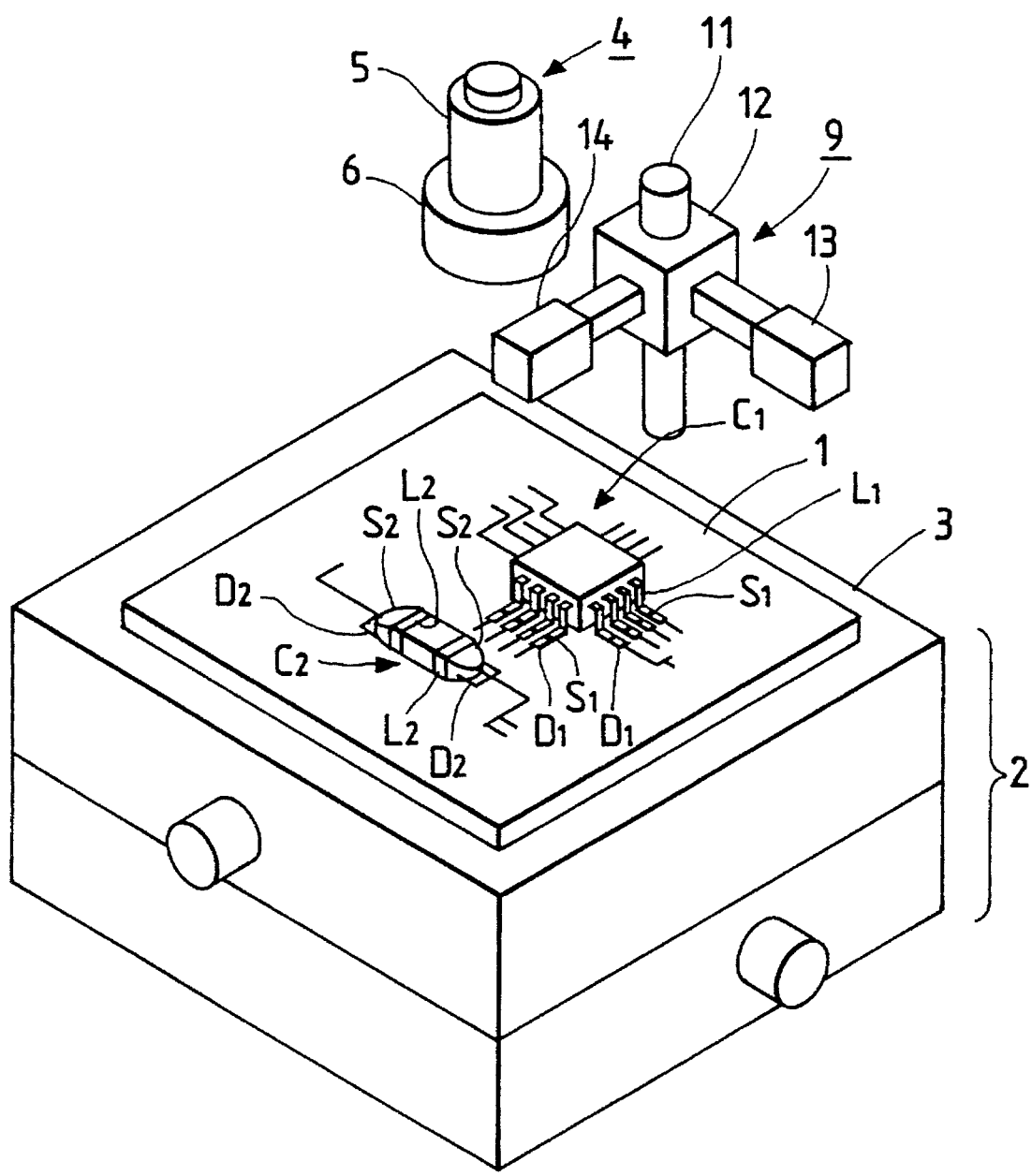
FIG. 1 is a perspective view of an apparatus for inspecting solder portion according to an embodiment of this invention.

With reference to FIG. 1, a circuit board 1 has an upper surface formed with an electric circuit pattern. Electronic components or parts are mounted on the upper surface of the circuit board 1 by solder portions. The electronic components include a flat-package electronic component C1 and a rectangular electronic component C2.

The flat-package electronic component C1 has a body, and a plurality of leads L1 horizontally extending from the body. Ends of the leads L1 are electrically and mechanically connected, via solder portions S1, to upper surfaces of electrodes D1 formed on the upper surface of the circuit board 1.

The rectangular electronic component C2 has a body, and leads L2 formed on opposite ends of the body. The leads L2 are electrically and mechanically connected, via solder portions S2, to upper surfaces of electrodes D2 formed on the upper surface of the circuit board 1.

The circuit board 1 is retained by a holder 3 attached to an upper portion of a horizontally-movable table 2 generally referred to as an XY table 2. The XY table 2 can move in two directions perpendicular to each other, that is, X and Y directions, on a horizontal plane. The XY table 2 can be driven by actuators 2A (not shown in FIG. 1, see FIG. 4). The circuit board 1 moves horizontally together with the XY table 2.

Figure 2:
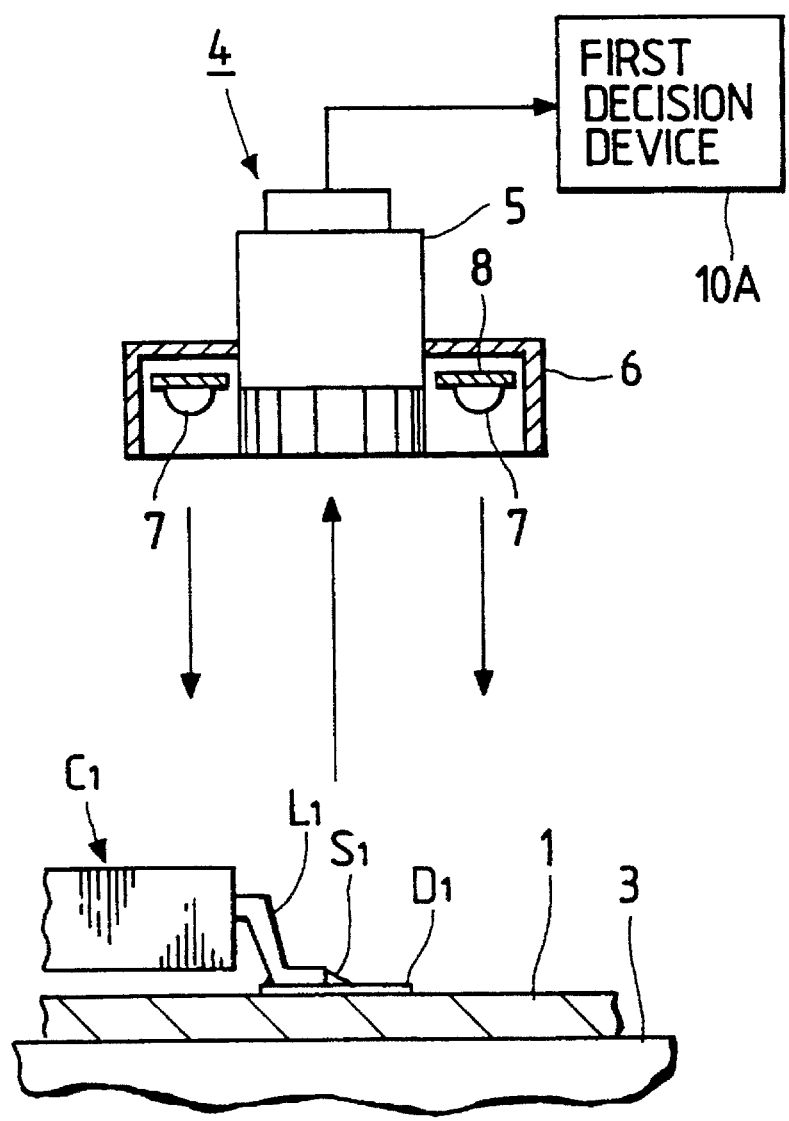
FIG. 2 is a sectional view of a circuit board and a camera arrangement in the apparatus of FIG. 1.

A camera arrangement 4 fixed by a suitable support (not shown) is located above the XY table 2, that is, above the circuit board 1. As shown in FIGS. 1 and 2, the camera arrangement 4 includes a camera 5, and a plurality of light-emitting elements 7 composing a light source. The light-emitting elements 7 are mounted on an annular base 8 fixedly extending around the body of the camera 5. The light-emitting elements 7 are arranged at equal intervals along a circumference around the body of the camera 5. A cylindrical cover 6 fixed to the body of the camera 5 houses the light-emitting elements 7 and the base 8. The cylindrical cover 6 has a closed upper end and an open lower end. The light-emitting elements 7 generate light which is applied to the circuit board 1 to illuminate the latter. The camera 5 converts an image of the circuit board 1 into a corresponding electric image signal. The image of the circuit board 1 includes images of the solder portions S1 and S2.

Figure 6:
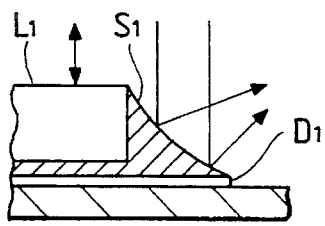
FIG. 6 is sectional view of a solder portion of a first type.
Figure 7:
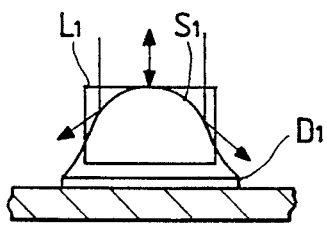
FIG. 7 is a front view of the solder portion in FIG. 6.
Figure 8:
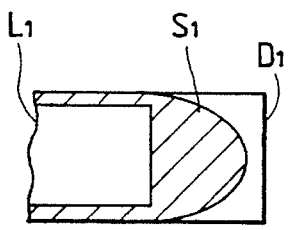
FIG. 8 is a top view of the solder portion in FIG. 6.

A description will now be given of typical types of a solder portion S1 (or S2). FIGS. 6, 7, and 8 show a solder portion S1 (or S2) of a type "A". As shown in FIG. 6, the solder portion S1 of the type "A" is adequately adapted to a lead L1 (or L2) with a good wettability, and therefore has a triangular section. As shown in FIG. 7, the solder portion S1 of the type "A" has a front side configuration similar to the shape of a knoll. Most of the light applied to the surfaces of the solder portion S1 of the type "A" from the light-emitting elements 7 is reflected toward inclined directions significantly deviating from the vertical upward direction so that it does not enter the camera 5. Therefore, as shown in FIG. 8, the solder portion S1 of the type "A" forms a dark area in the image obtained via the camera 5. On the other hand, the lead L1 forms a bright area in the image obtained via the camera 5 since the lead L1 has a flat upper surface.

Figure 9:
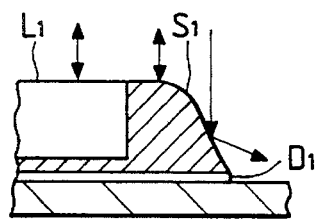
FIG. 9 is a sectional view of a solder portion of a second type.
Figure 10:
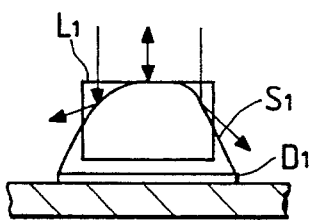
FIG. 10 is a front view of the solder portion in FIG. 9.
Figure 11:
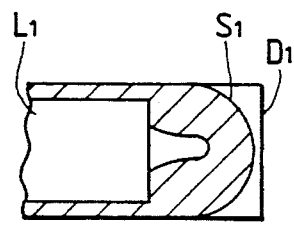
FIG. 11 is a top view of the solder portion in FIG. 9.

FIGS. 9, 10, and 11 show a solder portion S1 (or S2) of a type "B". As shown in FIGS. 9 and 10, a horizontal flat area extending from and being flush with an upper surface of a lead L1 (or L2) lies at a top of the solder portion S1 of the type "B". Most of the light applied to the flat area from the light-emitting elements 7 is reflected toward the vertical upward direction so that it enters the camera 5. Therefore, as shown in FIG. 11, the flat area forms a bright area in the image obtained via the camera 5. On the other hand, the solder portion S1 of the type "B" except the flat area forms a dark area in the image obtained via the camera 5. The bright area corresponding to the flat area extends from a bright area corresponding to the upper surface of the lead L1.

Figure 12:
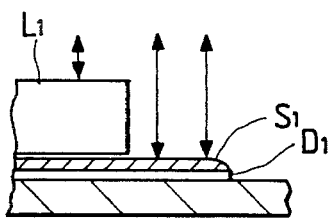
FIG. 12 is a sectional view of a solder portion of a third type.
Figure 13:
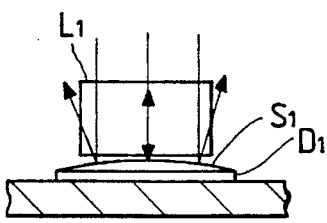
FIG. 13 is a front view of the solder portion in FIG. 12.
Figure 14:
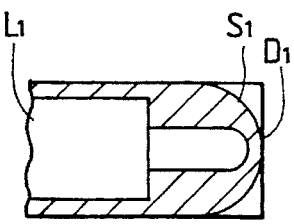
FIG. 14 is a top view of the solder portion in FIG. 12.

FIGS. 12, 13, and 14 show a solder portion S1 (or S2) of a type "C". As shown in FIGS. 12 and 13, the solder portion S1 of the type "C" is not bonded to a lead L1 (or L2). As shown in FIG. 13, the solder portion S1 of the type "C" has a front side configuration basically similar to the shape of a low hill or knoll. A top of the solder portion S1 of the type "C" is approximately flat, and is elongated along a horizontal plane. Most of the light applied to the top of the solder portion S1 of the type "C" from the light-emitting elements 7 is reflected toward the vertical upward direction so that it enters the camera 5. Therefore, as shown in FIG. 14, the top of the solder portion S1 of the type "C" forms an elongated bright area in the image obtained via the camera 5. On the other hand, the solder portion S1 of the type "C" except the top thereof forms a dark area in the image obtained via the camera 5.

Figure 15:
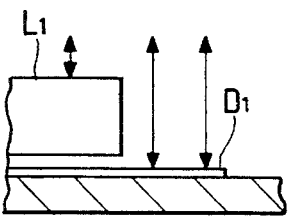
FIG. 15 sectional view of a solder portion of a fourth type.
Figure 16:
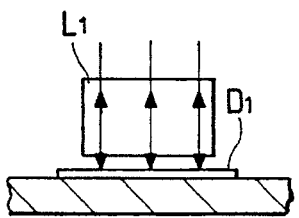
FIG. 16 is a front view of the solder portion in FIG. 15.
Figure 17:
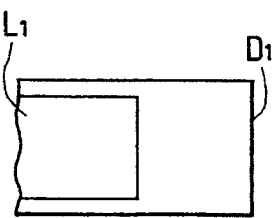
FIG. 17 is a top view of the solder portion in FIG. 15.

FIGS. 15, 16, and 17 show a solder portion S1 (or S2) of a type "D" which completely lacks solder. As shown in FIGS. 15 and 16, the solder portion S1 of the type "D" does not have any solder on an electrode D1 (or D2). Thus, an upper surface of the electrode D1 is exposed. Most of the light applied to the solder portion S1 of the type "D" from the light-emitting elements 7 is reflected at the upper surface of the electrode D1 toward the vertical upward direction so that it enters the camera 5. Therefore, as shown in FIG. 17, the solder portion S1 of the type "D" forms a bright area in the image obtained via the camera 5. The bright area corresponding to the solder portion S1 of the type "D" extends from a bright area corresponding to an upper surface of a lead L1 (or L2).

The solder portions S1 (and S2) of the types "A" and "B" are adequately bonded to the leads L1 (and L2). Thus, the solder portions S1 of the types "A" and "B" are satisfactory or good (all correct, OK). On the other hand, the solder portions S1 (and S2) of the types "C" and "D" are inadequately bonded to or fail to be bonded to the leads L1 (and L2). Thus, the solder portions S1 of the types "C" and "D" are unsatisfactory or no good (NG). The solder portions S1 of the types "A", "B", "C", and "D" correspond to respective typical solder portions which actually occur.

Figure 3:
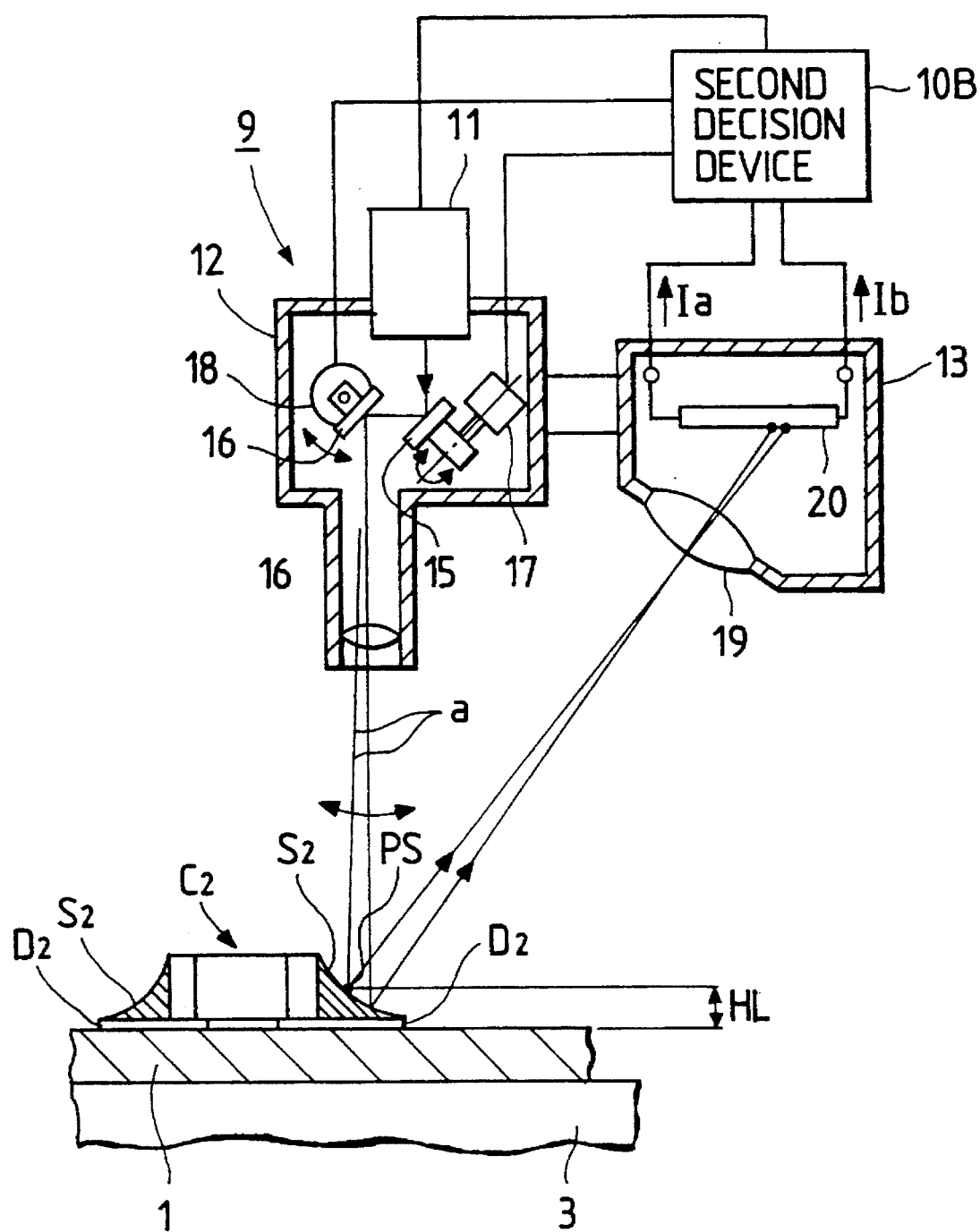
FIG. 3 is a sectional view of a circuit board and a height measurement device in the apparatus of FIG. 1.

As shown in FIG. 1, a height measurement device 9 includes a laser light source 11, a scanning section 12, and light receiving sections 13 and 14. As shown in FIG. 3, the scanning section 12 has a casing in which first mirror 15 and a second mirror 16 are disposed. The first mirror 15 is connected to a rotatable output shaft of a first actuator 17 so that the first mirror 15 can be rotated by the first actuator 17. The second mirror 16 is connected to a rotatable output shaft of a second actuator 18 so that the second mirror 16 can be rotated by the second actuator 18.

A laser light beam "a" emitted from the light source 11 is successively reflected by the first mirror 15 and the second mirror 16, being applied to a point PS of a surface of a solder portion S1 or S2 at approximately a right angle with respect to a horizontal plane of the circuit board 1. The laser light beam is reflected at or scattered by the point PS of the surface of the solder portion S1 or S2, and the reflected laser light beam reaches an optical position sensor 20 within the light receiving section 13 or 14 via a condenser lens 19.

The position of a spot of the laser light beam on the optical position sensor 20 depends on the height HL of the point PS of the surface of the solder portion S1 or S2 at which the laser light beam is reflected. The height HL is measured from an upper surface of the circuit board 1. The optical position sensor 20 detects the position of the spot of the laser light beam, and outputs, via its ends, signal currents Ia and Ib which have the following relation (1) with the height HL of the point PS of the surface of the solder portion S1 or S2:

$$HL = e \cdot \frac{Ia - Ib}{Ia + Ib} \quad (1)$$

where "e" denotes a predetermined constant.

The scanning section 12 enables the whole of the surface of the solder portion S1 or S2 and a region therearound to be scanned by the laser light beam. Specifically, the first and second mirrors 15 and 16 in the scanning section 12 are rotated by the first and second actuators 17 and 18 so that the laser light beam applied to the surface of the solder portion S1 or S2 moves relative to the surface of the solder portion S1 or S2.

As shown in FIG. 1, the light receiving sections 13 and 14 occupy places radially outward of the light source 11, and are spaced from each other by an angle of 90 degrees in a horizontal plane. The light receiving sections 13 and 14 have equal structures. The arrangement including the two light receiving sections 13 and 14 enables sure detection of the laser light beam reflected at the surface of a solder portion S1 or S2.

Figure 4:
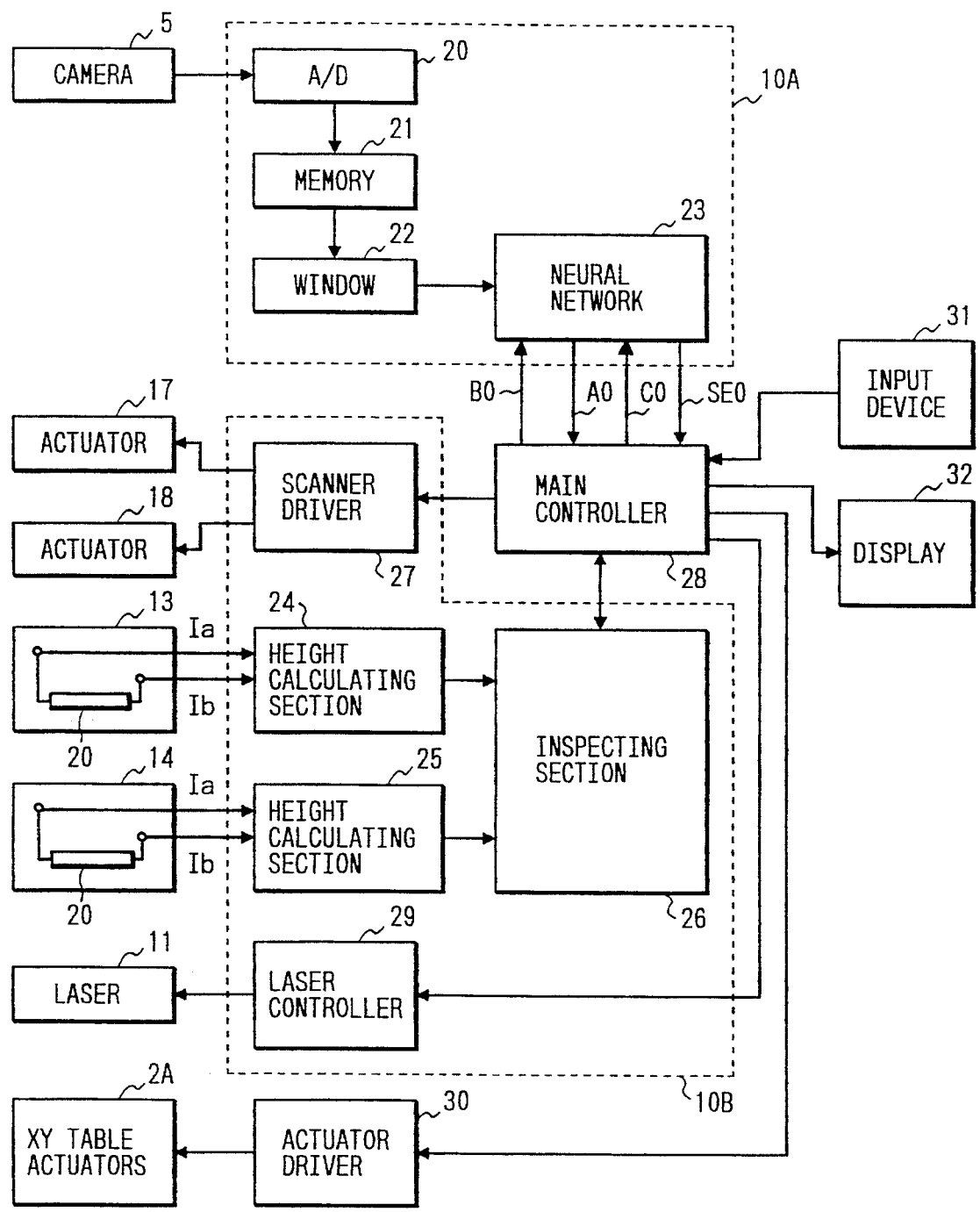
FIG. 4 is a block diagram of a portion of the apparatus of FIG. 1.

As shown in FIGS. 2 and 4, a first decision device 10A is electrically connected to the camera 5. The first decision device 10A includes an A/D converter 20, a memory 21, a window setting section 22, and a neural network system 23. The electric image signal outputted from the camera 5 is converted into a corresponding digital image signal by the A/D converter 20. The digital image signal outputted from the A/D converter 20 is stored into the memory 21. The image represented by the digital image signal stored in the memory 21 is of a gray scale type (a multiple-tone or halftone type). The window setting section 22 reads out only a portion of the digital image signal from the memory 21 as a window. In other words, the window setting section 22 selects a portion of the digital image signal in the memory 21 as a window. The selected portion of the digital image signal represents a part of the image, represented by the digital image signal, which contains a solder portion S1 or S2 to be inspected. Thus, a part of the image which contains a solder portion S1 or S2 to be inspected is selected as a window. The window setting section 22 includes, for example, a data selector. The selected window portion of the digital image signal is fed from the window setting section 22 to the neural network system 23.

With reference to FIGS. 2 and 3, a second decision device 10B includes height calculators 24 and 25, an inspecting section 26, a scanner driver 27, and a laser controller 29. The height calculator 24 receives signal currents Ia and Ib from the light receiving section 13. The height calculator 24 includes an A/D converter which converts signal currents Ia and Ib into corresponding digital signals. The height calculator 24 also includes a digital computing section receiving the output digital signals of the A/D converter which represent the signal currents Ia and Ib. The digital computing section calculates the height HL of a point PS of a surface of a solder portion S1 or S2 from the values of the signal currents Ia and Ib according to the previously-indicated equation (1). The digital computing section includes, for example, a programmable digital calculator. The digital computing section feeds the inspecting section 26 with a digital signal representing the calculated height HL of the point PS of the surface of the solder portion S1 or S2. The height calculator 25 receives signal currents Ia and Ib from the light receiving section 14. The height calculator 25 is equal in structure to the height calculator 24. The height calculator 25 converts the received signal currents Ia and Ib into a digital signal representing a calculated height HL of a point PS of a surface of a solder portion S1 or S2. The height calculator 25 feeds the digital height signal to the inspecting section 26.

The inspecting section 26 detects conditions of a solder portion S1 or S2 from the output height signals of the height calculators 24 and 25. The inspecting section 26 compares the detected conditions of the solder portion S1 or S2 with predetermined reference conditions to decide whether the solder portion S1 or S2 is acceptable or unacceptable (OK or NG).

The scanner driver 27 controls and drives the first and second actuators 17 and 18 of the scanning section 12 in response to an instruction signal outputted from a main controller 28. The laser controller 29 controls the laser light source 11 in response to a control signal outputted from the main controller 28.

The main controller 28 includes a combination of a processing section, a ROM, a RAM, and an interface. The main controller 28 operates in accordance with a program stored in the ROM. An actuator driver 30 connected to the main controller 28 controls and drives the XY table actuators 2A in response to a control signal outputted from the main controller 28. An input device 31 such as a keyboard connected to the main controller 28 is used in inputting information (data and signals) into the main controller 28. A display 32 connected to the main controller 28 serves to indicate information represented by an output signal of the main controller 28.

The neural network system 23 includes a CPU having a combination of a processing section, a ROM, and a RAM. The neural network system 23 operates in accordance with a program stored in the ROM. The neural network system 23 is of a hierarchical structure, having an input layer, a hidden layer (an intermediate layer), and an output layer.

Figure 5:
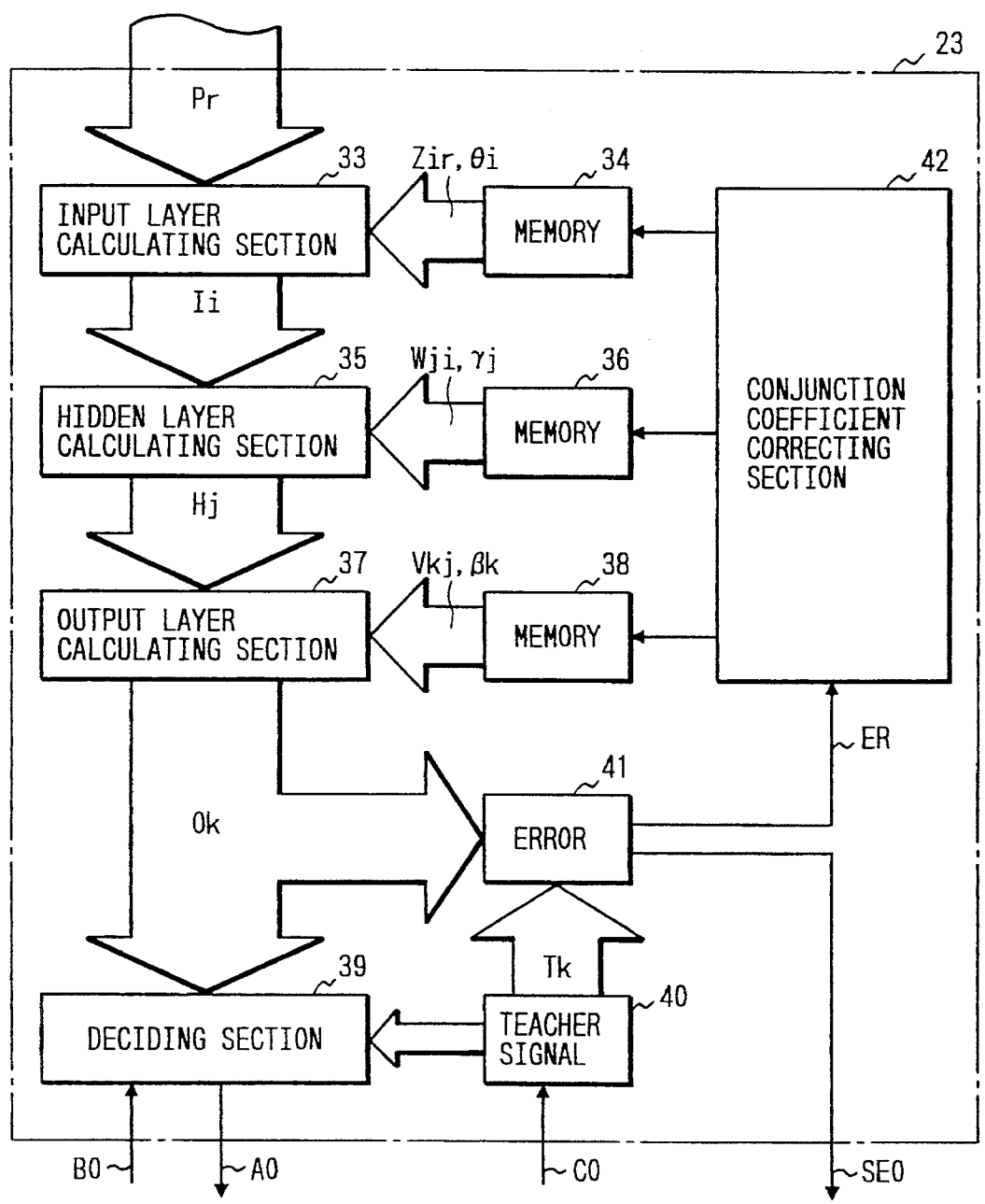
FIG. 5 is a signal flow diagram of a neural network system in the apparatus of FIG. 1.

FIG. 5 is a signal flow diagram of the neural network system 23. FIG. 5 does not directly show the hardware design of the neural network system 23. As shown in FIG. 5, the neural network system 23 includes an input-layer calculating section 33, a hidden-layer calculating section 35, an output-layer calculating section 37, and a deciding section 39.

The neural network system 23 operates as follows. The input-layer calculating section 33 receives the output signal of the window setting section 22 (see FIG. 4) which represents a window portion of an image of the circuit board 1. Generally, the window portion includes an image of a solder portion S1 or S2 to be inspected. One frame of the output signal of the window setting section 22 is composed of segments P1, P2, ..., Pr, ..., and Pro corresponding to pixels respectively, where "ro" denotes a predetermined natural number. The 1-frame output signal of the window setting section 22 is referred to as an input image signal Pr (r=1, 2, 3, ..., ro). The input-layer calculating section 33 generates or calculates an input-layer output signal Ii (i=1, 2, 3, ..., io) from the input image signal Pr by referring to the following equation:

$$Ii = f\left( \sum_r ZirPr + \theta i \right) \quad (2)$$

where f(x) denotes a predetermined threshold value function or sigmoid function; Zir denotes first conjunction coefficients; and θi denotes threshold values. It should be noted that "i" varies between 1 and a predetermined natural number "io". Data representing the first conjunction coefficients Zir and the threshold values θi are stored in a first memory section 34, and are fed to the input-layer calculating section 33 therefrom.

The hidden-layer calculating section 35 receives the input-layer output signal Ii from the input-layer calculating section 33. The hidden-layer calculating section 35 generates or calculates a hidden-layer output signal Hj (j=1, 2, 3, ..., jo) from the input-layer output signal Ii by referring to the following equation:

$$Hj = f\left( \sum_i WjiIi + \gamma j \right) \quad (3)$$

where Wji denotes second conjunction coefficients, and γj denotes threshold values. It should be noted that "j" varies between 1 and a predetermined natural number "jo". Data representing the second conjunction coefficients Wji and the threshold values γj are stored in a second memory section 36, and are fed to the hidden-layer calculating section 35 therefrom.

The output-layer calculating section 37 receives the hidden-layer output signal Hj from the hidden-layer calculating section 35. The output-layer calculating section 37 generates or calculates an output-layer output signal Ok (k=1, 2, 3, ..., ko) from the hidden-layer output signal Hj by referring to the following equation:

$$Ok = f\left(\sum_j VkjHj + \beta k\right) \quad (4)$$

where Vkj denotes third conjunction coefficients, and βk denotes threshold values. It should be noted that "k" varies between 1 and a predetermined natural number "ko". Data representing the third conjunction coefficients Vkj and the threshold values βk are stored in a third memory section 38, and are fed to the output-layer calculating section 37 therefrom.

The deciding section 39 receives the output-layer output signal Ok from the output-layer calculating section 37. The deciding section 39 determines whether the solder portion S1 or S2 which is currently inspected is good or poor (OK or NG) by referring to the output-layer output signal Ok.

The neural network system 23 can operate in either a learning mode or an image inspecting mode. In general, the learning mode of operation of the neural network system 23 is executed before the image inspecting mode of operation of the neural network system 23. During the learning mode of operation, the first conjunction coefficients Zir, the second conjunction coefficients Wji, and the third conjunction coefficients Vkj are determined according to a back-propagation algorithm.

The learning mode of operation of the neural network system 23 will now be described. A teacher signal output section 40 includes a memory section storing a given number of predetermined different teacher signals (Tk)A, (Tk)B, (Tk)C, (Tk)D, (Tk)E, . . . , and (Tk)Z. The teacher signal output section 40 selects and outputs one of the teacher signals (Tk)A–(Tk)Z in response to a control signal CO fed from the main controller 28 (see FIG. 4). As will be made clear later, the first, second, third, and fourth teacher signals (Tk)A, (Tk)B, (Tk)C, and (Tk)D are assigned to a solder portion S1 or S2 of the type "A", a solder portion S1 or S2 of the type "B", a solder portion S1 or S2 of the type "C", and a solder portion S1 or S2 of the type "D" respectively. The fifth and later teacher signals (Tk)E, . . . , and (Tk)Z are spares for solder portions S1 or S2 of types other than the types "A"–"D".

Figure 18:
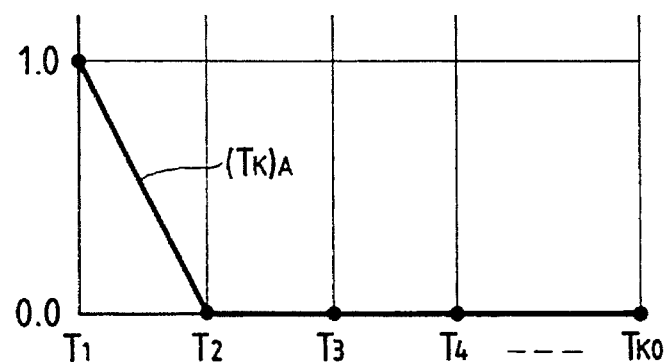
FIG. 18 is a diagram of the values of components of a first teacher signal.
Figure 19:
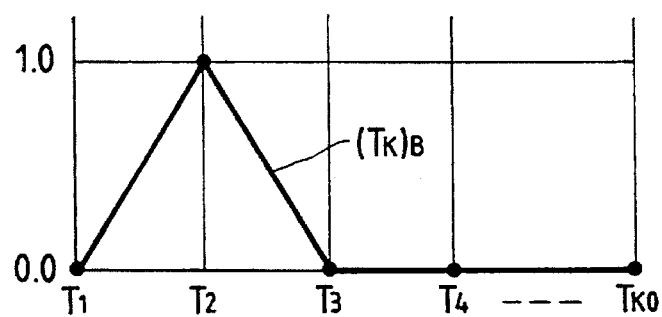
FIG. 19 is a diagram of the values of components of a second teacher signal.
Figure 20:
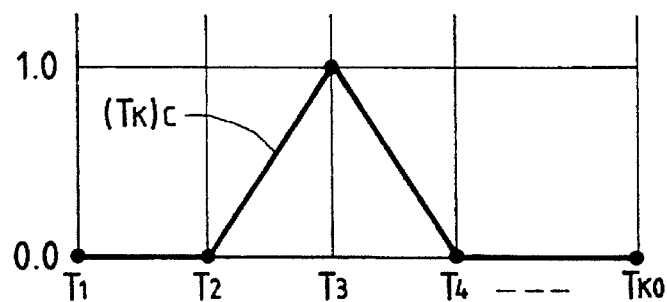
FIG. 20 is a diagram of the values of components of a third teacher signal.
Figure 21:
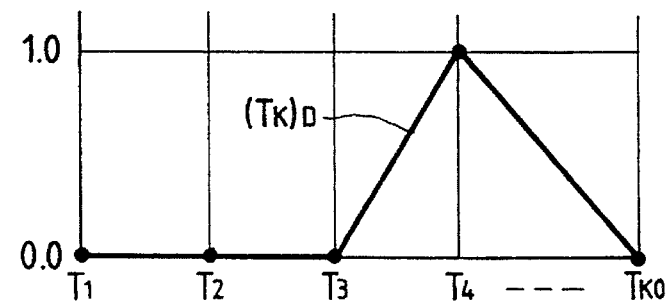
FIG. 21 is a diagram of the values of components of a fourth teacher signal.

For example, as shown in FIG. 18, the first teacher signal (Tk)A has a first component T1 corresponding to a value of 1.0 and other components T2, T3, . . . , Tko corresponding to a value of 0. As shown in FIG. 19, the second teacher signal (Tk)B has a second component T2 corresponding to a value of 1.0 and other components T1, T3, . . . , Tko corresponding to a value of 0. As shown in FIG. 20, the third teacher signal (Tk)C has a third component T3 corresponding to a value of 1.0 and other components T1, T2, T4, . . . , Tko corresponding to a value of 0. As shown in FIG. 21, the fourth teacher signal (Tk)D has a fourth component T4 corresponding to a value of 1.0 and other components T1, T2, T3, T5, . . . , Tko corresponding to a value of 0. As shown in FIG. 21, the fifth teacher signal (Tk)E has a fifth component T5 corresponding to a value of 1.0 and other components T1, . . . , T4, T6, . . . , Tko corresponding to a value of 0.

During the leaning mode of operation of the neural network system 23, an image of a typical solder portion S1 or S2 of the type "A" is actually taken via the camera 5. The neural network system 23 receives the output signal of the window setting section 22 which represents the image of the typical solder portion S1 or S2 of the type "A". The input-layer calculating section 33, the hidden-layer calculating section 35, and the output-layer calculating section 37 in the neural network system 23 execute the previously-mentioned calculating processes or signal processings so that the output-layer calculating section 37 generates an output-layer output signal Ok corresponding to the image of the typical solder portion S1 or S2 of the type "A". It should be noted that the conjunction coefficients Zir, Wji, and Vkj used in the calculating processes by the sections 33, 35, and 37 are previously set to given initial values.

An error calculating section 41 receives the output-layer output signal Ok from the output-layer calculating section 37. In addition, the input device 31 is operated to feed a control signal CO from the main controller 28 to the teacher signal output section 40. The teacher signal output section 40 selects and outputs the first teacher signal (Tk)A in response to the control signal CO. The error calculating section 41 receives the first teacher signal (Tk)A from the teacher signal output section 40. The error calculating section 41 calculates an error (an error signal) ER between the output-layer output signal Ok and the first teacher signal (Tk)A by referring to the following equation:

$$ER = \sum_k \frac{(Tk - Ok)^2}{2} \quad (5)$$

where Tk denotes the components of the first teacher signal (Tk)A. The error calculating section 41 informs a coefficient correcting section 42 of the calculated error ER.

The coefficient correcting section 42 corrects and updates the conjunction coefficients Zir, Wji, and Vkj in response to the calculated error ER in directions of decreasing the error ER. For example, the new conjunction coefficients Zir(NEW), Wji(NEW), and Vkj(NEW) are calculated from the previous conjunction coefficients Zir(OLD), Wji(OLD), and Vkj(OLD), and the error ER by referring to the following equations:

$$Zir(NEW) = Zir(OLD) - \alpha \cdot \frac{\partial E}{\partial Zir} \quad (6)$$

$$Wji(NEW) = Wji(OLD) - \alpha \cdot \frac{\partial E}{\partial Wji} \quad (7)$$

$$Vkj(NEW) = Vkj(OLD) - \alpha \cdot \frac{\partial E}{\partial Vkj} \quad (8)$$

where "α" denotes a predetermined constant. In the memory sections 34, 36, and 38, data representing the old conjunction coefficients Zir(OLD), Wji(OLD), and Vkj(OLD) are replaced by data representing the new conjunction coefficients Zir(NEW), Wji(NEW), and Vkj(NEW). Accordingly, the conjunction coefficients Zir, Wji, and Vkj in the memory sections 34, 36, and 38 are updated in response to the error ER.

Subsequently, the input-layer calculating section 33, the hidden-layer calculating section 35, and the output-layer calculating section 37 in the neural network system 23 execute the previously-mentioned calculating processes or signal processings while using the new conjunction coefficients Zir, Wji, and Vkj fed from the memory sections 34, 36, and 38. As a result, the output-layer calculating section 37 generates a new output-layer output signal Ok corresponding to the image of the typical solder portion S1 or S2 of the type "A". The error calculating section 41 calculates a new error (a new error signal) ER between the new output-layer output signal Ok and the first teacher signal (Tk)A in the previously-mentioned way. The coefficient correcting section 42 corrects and updates the conjunction coefficients Zir, Wji, and Vkj in response to the calculated new error ER in the previously-mentioned way.

The above-mentioned processes are reiterated until the calculated error ER between the output-layer output signal Ok and the first teacher signal (Tk)A falls into a predetermined allowable range. The error calculating section 41 includes a comparing section which decides whether or not the calculated error ER is in the allowable range. When the calculated error ER falls into the allowable range, the comparing section of the error calculating section 41 feeds the main controller 28 with a signal SE0 representing completion of the learning process on the image of the typical solder portion S1 or S2 of the type "A". Information of the completion of the learning process on the image of the typical solder portion S1 or S2 of the type "A" is transmitted via the main controller 28 to the display 32 to be indicated by the latter. The finally-available output-layer output signal Ok is adequately approximate to the first teacher signal (Tk)A.

After the learning process on the image of the typical solder portion S1 or S2 of the type "A" has been completed, a next learning process is started regarding an image of a typical solder portion S1 or S2 of the type "B". Specifically, an image of a typical solder portion S1 or S2 of the type "B" is actually taken via the camera 5. The neural network system 23 receives the output signal of the window setting section 22 which represents the image of the typical solder portion S1 or S2 of the type "B". In addition, the input device 31 is operated so that the second teacher signal (Tk)B will be selected in the neural network system 23. The neural network system 23 executes a learning process on the image of the typical solder portion S1 or S2 of the type "B" which is similar to the previously-mentioned learning process on the image of the typical solder portion S1 or S2 of the type "A". When the learning process on the image of the typical solder portion S1 or S2 of the type "B" is completed, that is, when the calculated error ER falls into the allowable rage, the neural network system 23 feeds the main controller 28 with a signal SE0 representing completion of the learning process on the image of the typical solder portion S1 or S2 of the type "B". Information of the completion of the learning process on the image of the typical solder portion S1 or S2 of the type "B" is transmitted via the main controller 28 to the display 32 to be indicated by the latter. The finally-available output-layer output signal Ok is adequately approximate to the second teacher signal (Tk)B.

After the learning process on the image of the typical solder portion S1 or S2 of the type "B" has been completed, a next learning process is started regarding an image of a typical solder portion S1 or S2 of the type "C". Specifically, an image of a typical solder portion S1 or S2 of the type "C" is actually taken via the camera 5. The neural network system 23 receives the output signal of the window setting section 22 which represents the image of the typical solder portion S1 or S2 of the type "C". In addition, the input device 31 is operated so that the third teacher signal (Tk)C will be selected in the neural network system 23. The neural network system 23 executes a learning process on the image of the typical solder portion S1 or S2 of the type "C" which is similar to the previously-mentioned learning process on the image of the typical solder portion S1 or S2 of the type "A". When the learning process on the image of the typical solder portion S1 or S2 of the type "C" is completed, that is, when the calculated error ER falls into the allowable range, the neural network system 23 feeds the main controller 28 with a signal SE0 representing completion of the learning process on the image of the typical solder portion S1 or S2 of the type "C". Information of the completion of the learning process on the image of the typical solder portion S1 or S2 of the type "C" is transmitted via the main controller 28 to the display 32 to be indicated by the latter. The finally-available output-layer output signal Ok is adequately approximate to the third teacher signal (Tk)C.

After the learning process on the image of the typical solder portion S1 or S2 of the type "C" has been completed, a next learning process is started regarding an image of a typical solder portion S1 or S2 of the type "D". Specifically, an image of a typical solder portion S1 or S2 of the type "D" is actually taken via the camera 5. The neural network system 23 receives the output signal of the window setting section 22 which represents the image of the typical solder portion S1 or S2 of the type "D". In addition, the input device 31 is operated so that the fourth teacher signal (Tk)D will be selected in the neural network system 23. The neural network system 23 executes a learning process on the image of the typical solder portion S1 or S2 of the type "D" which is similar to the previously-mentioned learning process on the image of the typical solder portion S1 or S2 of the type "A". When the learning process on the image of the typical solder portion S1 or S2 of the type "D" is completed, that is, when the calculated error ER falls into the allowable range, the neural network system 23 feeds the main controller 28 with a signal SE0 representing completion of the learning process on the image of the typical solder portion S1 or S2 of the type "D". Information of the completion of the learning process on the image of the typical solder portion S1 or S2 of the type "D" is transmitted via the main controller 28 to the display 32 to be indicated by the latter. The finally-available output-layer output signal Ok is adequately approximate to the fourth teacher signal (Tk)D.

As previously described, the image inspecting mode of operation of the neural network system 23 is executed after the learning mode of operation of the neural network system 23 has been completed. During the image inspecting mode of operation of the neural network system 23, an image of a solder portion S1 or S2 to be inspected is actually taken via the camera 5. The image of the solder portion S1 or S2 to be inspected is referred to as the image of the currently-inspected solder portion S1 or S2. The neural network system 23 receives the output signal of the window setting section 22 which represents the image of the currently-inspected solder portion S1 or S2.

The input-layer calculating section 33, the hidden-layer calculating section 35, and the output-layer calculating section 37 in the neural network system 23 execute the previously-mentioned calculating processes or signal processings while using the conjunction coefficients Zir, Wji, and Vkj fed from the memory sections 34, 36, and 38. As a result, the output-layer calculating section 37 generates an output-layer output signal Ok corresponding to the image of the currently-inspected solder portion S1 or S2.

Figure 28:
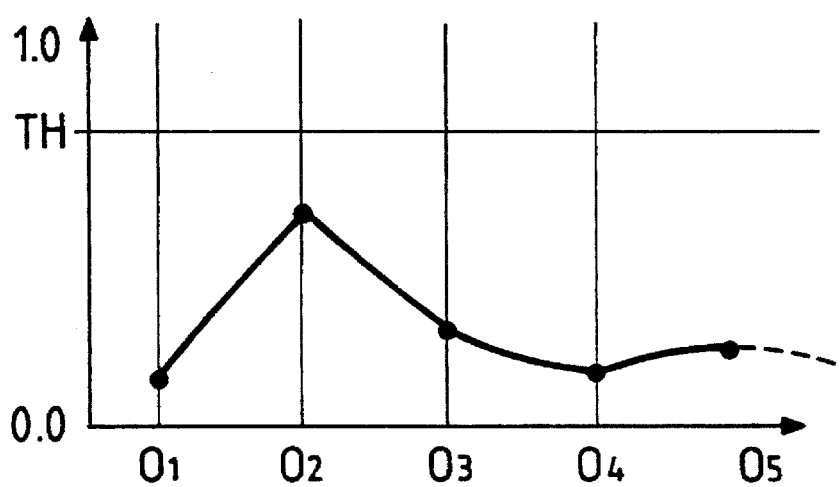
FIG. 28 is a diagram showing the values of components of an example of an output-layer output signal in the neural network system of FIG. 5.

In the neural network system 23, the deciding section 39 starts to operate in response to a control signal fed from the main controller 28. For example, the control signal is outputted from the main controller 28 when the input device 31 is operated to instruct start of the image inspecting mode of operation of the neural network system 23. The deciding section 39 receives the output-layer output signal Ok from the output-layer calculating section 37. The deciding section 39 compares each component of the output-layer output signal Ok with a predetermined threshold value TH in the range of 0.8 to 0.9. It should be noted that each component of the output-layer output signal Ok is generally variable between 0 and 1.0. When all the components of the output-layer output signal Ok are equal to or smaller than the threshold valve TH as shown in FIG. 28, the deciding section 39 determines the currently-inspected solder portion S1 or S2 to be gray (GRAY). Otherwise, the deciding section 39 subsequently executes a pattern matching process as will be described below. The gray (GRAY) determination means that the currently-inspected solder portion S1 or S2 is of a type other than the types "A", "B", "C", and "D".

In the neural network system 23, the teacher signal output section 40 informs the deciding section 39 of the first, second, third, and fourth teacher signals (Tk)A, (Tk)B, (Tk)C, and (Tk)D. The deciding section 39 determines which of the first, second, third, and fourth teacher signals (Tk)A, (Tk)B, (Tk)C, and (Tk)D the output-layer output signal Ok is closest to by using a known pattern matching algorithm. In other words, the deciding section 39 determines which of the types "A", "B", "C", and "D" the currently-inspected solder portion S1 or S2 belongs to. When the closest teacher signal agrees with the first teacher signal (Tk)A, that is, when the currently-inspected solder portion S1 or S2 is of the type "A", the deciding section 39 determines the currently-inspected solder portion S1 or S2 to be satisfactory or good (all correct, OK). When the closest teacher signal agrees with the second teacher signal (Tk)B, that is, when the currently-inspected solder portion S1 or S2 is of the type "B", the deciding section 39 determines the currently-inspected solder portion S1 or S2 to be satisfactory or good (all correct, OK). When the closest teacher signal agrees with the third teacher signal (Tk)C, that is, when the currently-inspected solder portion S1 or S2 is of the type "C", the deciding section 39 determines the currently-inspected solder portion S1 or S2 to be unsatisfactory or no good (NG). When the closest teacher signal agrees with the fourth teacher signal (Tk)D, that is, when the currently-inspected solder portion S1 or S2 is of the type "D", the deciding section 39 determines the currently-inspected solder portion S1 or S2 to be unsatisfactory or no good (NG).

In this way, the deciding section 39 executes a determination regarding the type of the currently-inspected solder portion S1 or S2. Furthermore, the deciding section 39 executes a determination regarding whether the currently-inspected solder portion S1 or S2 is GRAY, OK, or NG, that is, a determination regarding conditions of the currently-inspected solder portion S1 or S2. The deciding section 39 outputs an inspection result signal A0 to the main controller 28 which represents the determined type and the determined conditions of the currently-inspected solder portion S1 or S2. The main controller 28 stores the inspection result signal A0 into an internal RAM.

The way of determining whether or not the currently-inspected solder portion S1 or S2 is gray (GRAY) may be executed as follows. First, an error ERA between the output-layer output signal Ok and the first teacher signal (Tk)A is calculated by referring an equation similar to the equation (5). Then, calculation is also given of an error ERB between the output-layer output signal Ok and the second teacher signal (Tk)B, an error ERC between the output-layer output signal Ok and the third teacher signal (Tk)C, and an error ERD between the output-layer output signal Ok and the fourth teacher signal (Tk)D. The calculated errors ERA, ERB, ERC, and ERD are compared with each other to determine a minimum error therefrom. The minimum error is compared with a predetermined reference error. When the minimum error exceeds the reference error, the currently-inspected solder portion S1 or S2 is determined to be gray (GRAY).

Also, the second decision device 10B and the associated devices operate to inspect a solder portion S1 or S2 on the circuit board 1. As will be made clear later, the inspection by the second decision device 10B is designed to supplement the inspection by the first decision device 10A.

Figure 22:
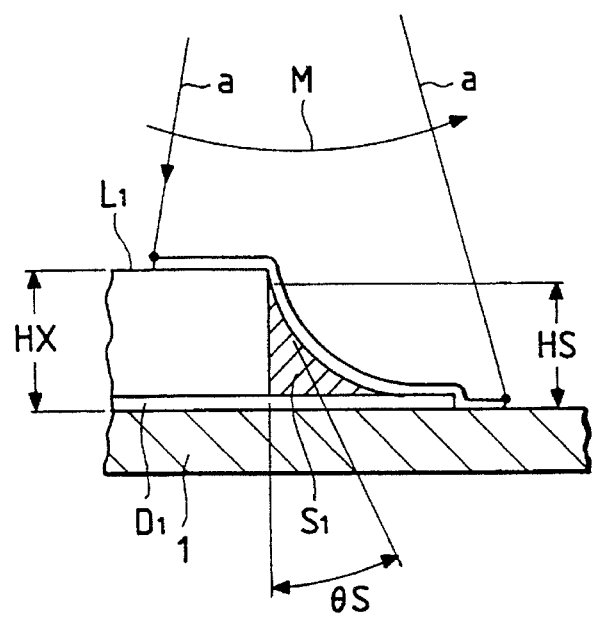
FIG. 22 sectional view of a part of a circuit board.

Operation of the second decision device 10B and the associated devices will now be described. First, the main controller 28 controls the XY table actuators 2A via the actuator driver 30 so that a solder portion S1 or S2 to be inspected will be moved to a position directly below the height measurement device 9. The solder portion S1 or S2 to be inspected is referred to as the currently-inspected solder portion S1 or S2. Second, the main controller 28 controls the first and second actuators 17 and 18 of the scanning section 12 via the scanner driver 27 so that an upper surface of the currently-inspected solder portion S1 or S2 and a region therearound will be scanned by the laser light beam emitted from the light source 11. Specifically, as shown in FIG. 22, the laser light beam "a" is moved or deflected in a main scanning direction "M" so that a spot of the laser light beam moves from an upper surface of a lead L1 or L2 to an exposed upper surface of a circuit board 1 via the upper surface of the currently-inspected solder portion S1 or S2 and an exposed upper surface of an electrode D1 or D2. In this way, a 1-line part of the upper surfaces of the lead L1 or L2, the currently-inspected solder portion S1 or S2, the electrode D1 or D2, and the circuit board 1 is scanned by the laser light beam. Such a 1-line scanning process is periodically reiterated while the laser light beam is periodically moved step by step along a sub scanning direction perpendicular to the main scanning direction "M". As a result, the whole of the upper surface of the currently-inspected solder portion S1 or S2, and also regions of the upper surfaces of the lead L1 or L2, the electrode D1 or D2, and the circuit board 1 which extend around the currently-inspected solder portion S1 or S2 are scanned by the laser light beam.

During the above-mentioned scanning process, the laser light beam is reflected at or scattered by the upper surfaces of the lead L1 or L2, the currently-inspected solder portion S1 or S2, the electrode D1 or D2, and the circuit board 1. The reflected laser light beam reaches the optical position sensor 20 within the light receiving section 13 or 14 via the condenser lens 19. As previously described, the optical position sensor 20 outputs the signal currents Ia and Ib which represent the height of the currently-illuminated point on the upper surfaces of the lead L1 or L2, the currently-inspected solder portion S1 or S2, the electrode D1 or D2, and the circuit board 1. The height calculators 24 and 25 derive or calculate the height of the currently-illuminated point from the signal currents Ia and Ib outputted from the optical sensors 20 in the light receiving sections 13 and 14. The height calculators 24 and 25 output signals representative of the calculated height to the inspecting section 26.

The inspecting section 26 decides whether the currently-inspected solder portion S1 or S1 is satisfactory (acceptable, OK) or poor (unacceptable, NG) in response to the output height signals of the height calculators 24 and 25. The inspecting section 26 includes a CPU having a combination of a processing section, a ROM, and a RAM. The inspecting section 26 operates in accordance with a program stored in the ROM.

First, the inspecting section 26 detects a maximum height HS of the currently-inspected solder portion S1 or S2 by referring to the output height signals of the height calculators 24 and 25. The maximum height HS is measured from the upper surface of the circuit board 1. The inspecting section 26 compares the maximum height HS with reference heights 0.9 HX and 1.1 HX to decide whether or not the maximum height HS is in a range between 0.9 HX and 1.1 HX, where HX denotes a height of the lead L1 or L2. When the maximum height HS is outside the range between 0.9 HX and 1.1 HX, the inspecting section 26 decides the currently-inspected solder portion S1 or S2 to be poor (unacceptable, NG). Subsequently, the inspecting section 26 calculates an average angle θs formed between the vertical surface of the lead L1 or L2 and the upper surface of the currently-inspected solder portion S1 and S2. Since the angle θs depends on the wettability of the currently-inspected solder portion S1 or S2 with respect to the lead L1 or L2, the angle θs is referred to as the wettability angle. The inspecting section 26 compares the calculated wettability angle θs with a predetermined minimum allowable wettability angle θmin. When the wettability angle θs is smaller than the minimum allowable wettability angle θmin, the inspecting section 26 decides the currently-inspected solder portion S1 or S2 to be poor (unacceptable, NG). On the other hand, when the maximum height HS is in the range between 0.9 HX and 1.1 HX and also the wettability angle θs is equal to or greater than the minimum allowable wettability angle θmin, the inspecting section 26 decides the currently-inspected solder portion S1 or S2 to be good (acceptable, OK). The inspecting section 26 generates and outputs an inspection result signal representing whether the currently-inspected solder portion S1 or S2 is OK or NG. The inspecting section 26 feeds the inspection result signal to the main controller 28. The main controller 28 transmits the inspection result signal to the neural network system 23 in the first decision device 10A as an output signal B0 therefrom.

As previously described, the second decision device 10B derives the maximum height HS of the currently-inspected solder portion S1 or S2 and also the wettability angle θs from the height signals, and executes the inspection in response to the maximum height HS and the wettability angle θs. Accordingly, the inspection by the second decision device 10B is applicable to a solder portion S1 or S2 of any type. In other words, the inspection by the second decision device 10B is applicable to a solder portion S1 or S2 of a type other than the types "A", "B", "C", and "D".

Figure 23:
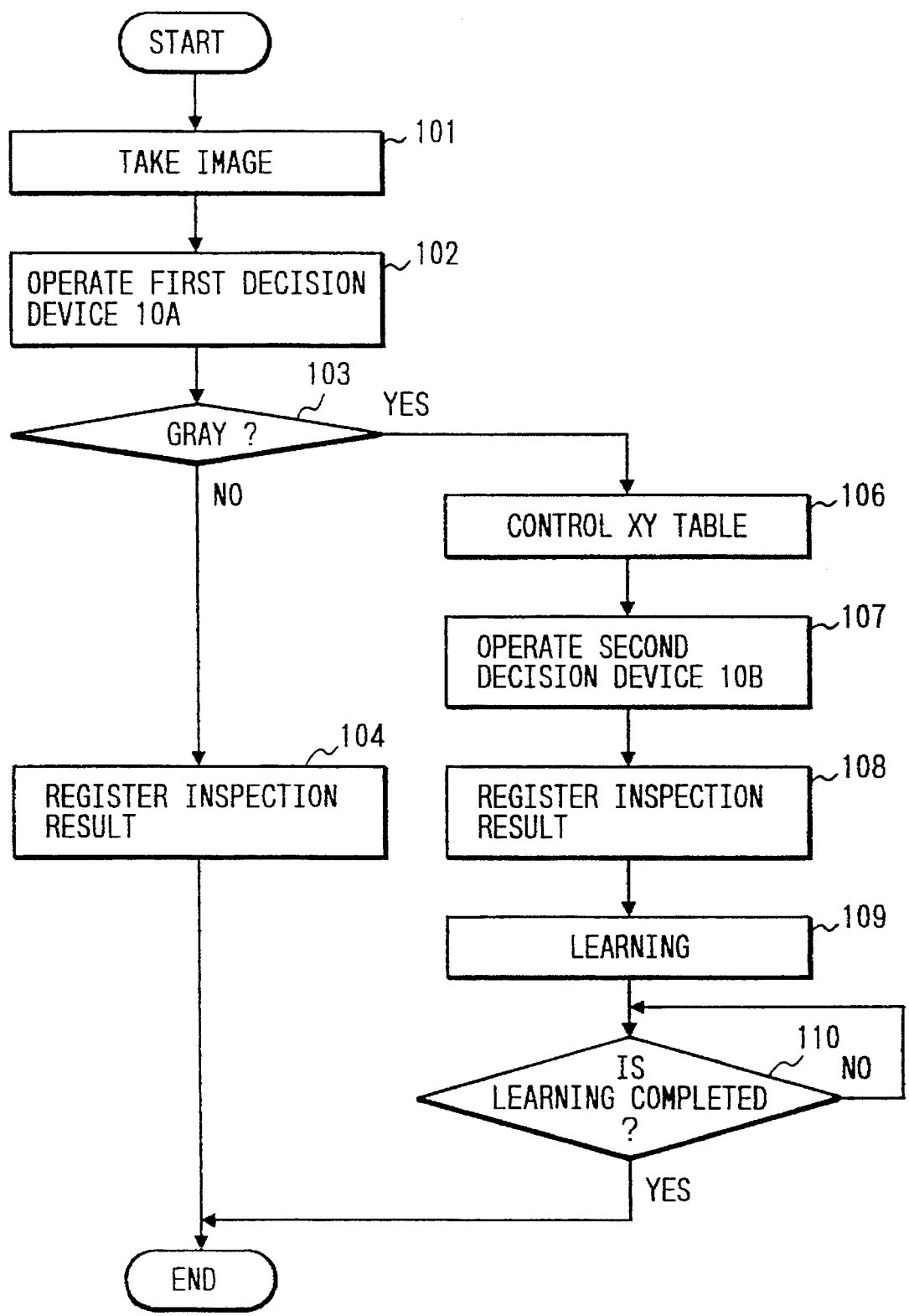
FIG. 23 is a flowchart of a part of a program for controlling a main controller in the apparatus of FIG. 1.

As previously described, the main controller 28 operates in accordance with a program stored in the internal ROM. FIG. 23 is a flowchart of a segment of this program which is executed for each of solder portions S1 and S2 on a circuit board 1.

As shown in FIG. 23, a first step 101 of the program segment controls the XY table actuators 2A via the actuator driver 30 in response to predetermined information of positions of solder portions S1 and S2 on a circuit board 1 so that one of the solder portions S1 and S2 will be moved to a place directly below the camera 5. It should be noted that the information of the positions of the solder portions S1 and S2 is previously stored in the ROM or RAM within the main controller 28. A solder portion S1 or S2 at a place directly below the camera 5 is a solder portion S1 or S2 to be inspected, that is, a currently-inspected solder portion S1 or S2. An image of the circuit board 1 which includes an image of the currently-inspected solder portion S1 or S2 is taken via the camera 5.

A step 102 following the step 101 controls the first decision device 10A so that the first decision device 10A will operate in the image inspecting mode. As previously described, the first decision device 10A determines whether the currently-inspected solder portion S1 or S2 is OK, NG, or GRAY in response to the output image signal of the camera 5. The first decision device 10A outputs the determination result signal (the inspection result signal) to the main controller 28.

A step 103 following the step 102 decides whether or not the currently-inspected solder portion S1 or S2 is GRAY by referring to the inspection result signal A0 from the first decision device 10A. When the currently-inspected solder portion S1 or S2 is not GRAY, the program advances from the step 103 to a step 104. When the currently-inspected solder portion S1 or S2 is GRAY, the program advances from the step 103 to a step 106.

The step 104 stores or registers the inspection result signal (the output signal of the first decision device 10A) into the RAM within the main controller 28. After the step 104, the program segment ends.

The step 106 controls the XY table actuators 2A via the actuator driver 30 in response to the predetermined information of the position of the currently-inspected solder portion S1 or S2 so that the currently-inspected solder portion S1 or S2 will be moved to a place directly below the height measurement device 9.

A step 107 following the step 106 activates the second decision device 10B and also the height measurement device 9 including the laser light source 11. As previously described, the optical position sensors 20 in the height measurement device 9 output the height signals to the second decision device 10B. The second decision device 10B determines whether the currently-inspected solder portion S1 or S2 is OK or NG in response to the output signals from the height measurement device 9. The second decision device 10B outputs the determination result signal (the inspection result signal) to the main controller 28.

A step 108 following the step 107 stores or registers the inspection result signal (the output signal of the second decision device 10B) into the RAM within the main controller 28. After the step 108, the program advances to a step 109.

The step 109 transmits the inspection result signal B0 (the output signal of the second decision device 10B) to the neural network system 23 in the first decision device 10A. In addition, the step 109 controls the XY table actuators 2A via the actuator driver 30 in response to the predetermined information of the position of the currently-inspected solder portion S1 or S2 so that the currently-inspected solder portion S1 or S2 will be moved to a place directly below the camera 5. An image of the circuit board 1 which includes an image of the currently-inspected solder portion S1 or S2 is taken via the camera 5. Furthermore, the step 109 controls the first decision device 10A so that the first decision device 10A will operate in the learning mode. The step 109 outputs a control signal CO to the first decision device 10A to select one of the spare teacher signals (Tk)E, . . . , (Tk)Z.

During the learning mode of operation of the first decision device 10A, the neural network system 23 receives the output signal of the window setting section 22 which represents the image of the currently-inspected solder portion S1 or S2. One of the spare teacher signals (Tk)E, . . . , (Tk)Z stored in the teacher signal output section 40 is selected in response to the control signal CO fed from the main controller 28. For example, the fifth teacher signal (Tk)E is selected. The neural network system 23 executes a learning process on the image of the currently-inspected solder portion S1 or S2 which is similar to the previously-mentioned learning processes on the images of the typical solder portions S1 or S2 of the types "A", "B", "C", and "D". When the learning process on the image of the currently-inspected solder portion S1 or S2 is completed, that is, when the calculated error ER falls into the allowable range, the neural network system 23 feeds the main controller 28 with a signal SE0 representing completion of the learning process on the image of the currently-inspected solder portion S1 or S2.

After the step 109, the program advances to a step 110. The step 110 detects whether or not the learning process on the image of the currently-inspected solder portion S1 or S2 is completed by referring to the output signal SE0 from the first decision device 10A. When the learning process on the image of the currently-inspected solder portion S1 or S2 is not completed, the step 109 is repeated. When the learning process on the image of the currently-inspected solder portion S1 or S2 is completed, the program segment ends.

As previously described, when a currently-inspected solder portion S1 or S2 is determined to be GRAY by the first decision device 10A, the second decision device 10B is activated to determine whether the currently-inspected solder portion S1 or S2 is OK or NG. The information of whether the currently-inspected solder portion S1 or S2 is OK or NG is transmitted from the second decision device 10B to the first decision device 10A via the main controller 28. In addition, operation of the first decision device 10A is changed from the image inspecting mode to the learning mode. Thus, the learning process is executed on the currently-inspected solder portion S1 or S2. Regarding the learning process, one of the spare teacher signals, for example, the fifth spare signal (Tk)E, is assigned to a type of the currently-inspected solder portion S1 or S2 which differs from the types "A", "B", "C", and "D". As a result of the learning process, the first decision device 10A is reconstructed to additionally sense a new type of a solder portion which is similar to the type of the currently-inspected solder portion S1 or S2. This means that the type of the currently-inspected solder portion S1 or S2 is registered in the first decision device 10A as a typical solder portion of a new type "E" different from the types "A", "B", "C", and "D". In addition, the information of whether the currently-inspected solder portion S1 or S2 is OK or NG is used as information representing whether a typical solder portion of the type "E" is OK or NG which is registered in the first decision device 10A. The fifth teacher signal (Tk)E is made related to the type "E" in the first decision device 10A. Accordingly, the inspection of next and later solder portions S1 and S2 by the first decision device 10A refers to the teacher signals (Tk)A, (Tk)B, (Tk)C, (Tk)D, and (Tk)E and the related types "A", "B", "C", "D", and "E".

Figure 24:
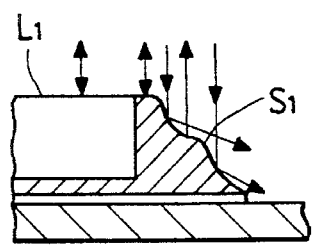
FIG. 24 is a sectional view of a solder portion of a fifth type.
Figure 25:
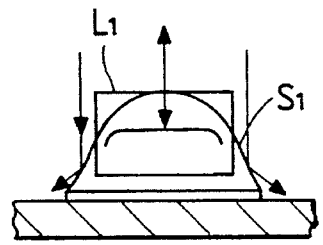
FIG. 25 is a front view of the solder portion in FIG. 24.
Figure 26:
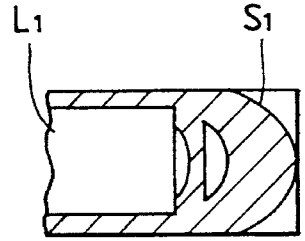
FIG. 26 is a top view of the solder portion in FIG. 24.

FIGS. 24, 25, and 26 show an example of a solder portion S1 (or S2) of the type "E". As shown in FIGS. 24 and 25, the solder portion S1 of the type "E" has a two-stage or two-step configuration. A horizontal flat area extends in and around a center of the solder portion S1 of the type "E". Most of the light applied to the flat area from the light-emitting elements 7 is reflected toward the vertical upward direction so that it enters the camera 5. Therefore, as shown in FIG. 26, the flat area forms a semicircular bright area in the image obtained via the camera 5. On the other hand, the solder portion S1 of the type "E" except the flat area forms a dark area in the image obtained via the camera 5. The bright area corresponding to the flat area extends within the dark area corresponding to the rest of the solder portion S1 of the type "E".

Figure 27:
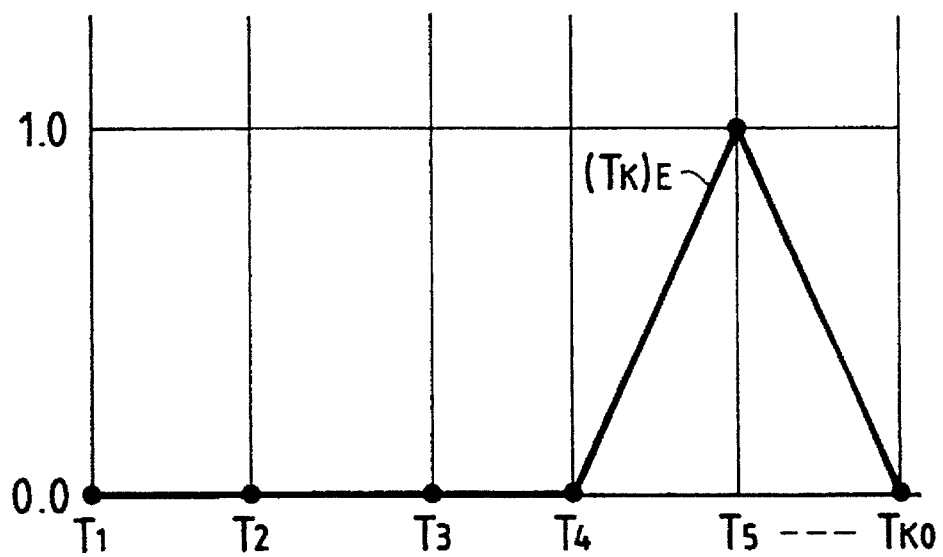
FIG. 27 is a diagram of values of components of a fifth teacher signal.

For example, as shown in FIG. 27, the fifth teacher signal (Tk)E has a fifth component T5 corresponding to a value of 1.0 and other components T1, . . . , T4, T6, . . . , Tko corresponding to a value of 0.

What is claimed is:

1. An apparatus comprising:

image taking means for taking an image of an object to be inspected, and outputting an image signal representative thereof;

first deciding means for deciding a condition of the object in response to the image signal and for executing a learning process;

measuring means for measuring a height of the object, and outputting a height signal representative of a height of the object;

second deciding means for deciding a condition of the object in response to the height signal; and control means for, in cases where the first deciding means can not decide the condition of the object, enabling the measuring means to measure the height of the object and enabling the second deciding means to decide the condition of the object, and enabling the first deciding means to execute the learning process on the object in response to a result of the decision by the second deciding means.

2. The apparatus of claim 1, wherein the first deciding means comprises:

memory means for storing the image signal outputted by the image taking means;

extracting means for extracting a portion of the image signal stored in the memory means which corresponds to the object, and outputting a partial image signal representative thereof; and condition deciding means for deciding the condition of the object in response to the partial image signal.

3. The apparatus of claim 2, wherein the condition deciding means comprises a neural network system.

4. The apparatus of claim 2, wherein the condition deciding means comprises:

an input-layer calculating section for calculating an input-layer output signal in response to the partial image signal and to first conjunction coefficients, and outputting the input-layer output signal;

a hidden-layer calculating section for calculating a hidden-layer output signal in response to the input-layer output signal and to second conjunction coefficients, and outputting the hidden-layer output signal;

an output-layer calculating section for calculating an output-layer output signal in response to the hidden-layer output signal and to third conjunction coefficients, and outputting the output-layer output signal;

a deciding section for deciding the condition of the object in response to the output-layer output signal;

a memory section for storing the first, second, and third conjunction coefficients; and a correcting section for correcting the first, second, and third conjunction coefficients.

5. The apparatus of claim 1, wherein the image taking means comprises a camera, and a light source for applying light to the object.

6. The apparatus of claim 1, wherein the measuring means comprises an illuminating section for applying light to the object, and a light receiving section for receiving light reflected by a surface of the object.

7. The apparatus of claim 1, wherein the object comprises a solder portion.

8. A method comprising the steps of:

taking an image of an object to be inspected;

first deciding a condition of the object in response to the image;

measuring a shape of the object to derive height information representing a height of the object in cases where a result of the decision by the first deciding step is gray; and second deciding a condition of the object in response to the height information;

wherein the first deciding step comprises executing a learning process on the object in response to a result of the decision by the second deciding step.

9. The method of claim 8, wherein the first deciding step comprises using a neural network system for the leaning process, and correcting conjunction coefficients in the neural network system during the learning process.

10. The apparatus of claim 8, wherein the object comprises a solder portion.

11. An apparatus for inspecting a solder portion, comprising:

first means for deciding whether or not an image of a solder portion being inspected is similar to one of images of typical solder portions and deciding whether the inspected solder portion is acceptable or unacceptable, said first means further having an ability to include additional images as images of additional typical solder portions;

second means connected to the first means for deciding whether the inspected solder portion is acceptable or unacceptable to supplement the decision by the first means when the first means decides the image of the inspected solder portion to be not similar to one of the images of the typical solder portions; and third means connected to the first means for, when the first means decides the image of the inspected solder portion to be not similar to one of the images of the typical solder portions, enabling the first means to include the image of the inspected solder portion as an image of an additional typical solder portion of said images of typical solder portions used by the first means, and adding the image of the inspected solder portion to said images of typical solder portions as an image of a new typical solder portion.

12. The apparatus of claim 11, wherein the first means and the third means comprise a CPU forming a neural network model.

13. An apparatus for inspecting a solder portion, comprising:

first means for determining whether or not an image of a solder portion being inspected is similar to one of a plurality of images of typical solder portions each corresponding to either an acceptable solder portion or an unacceptable solder portion, said first means further having an ability to include additional images as images of additional typical solder portions;

second means connected to the first means for deciding the inspected solder portion to be acceptable when the first means determines the image of the inspected solder portion to be similar to one of the images of typical solder portions each corresponding to an acceptable solder portion, and for deciding the inspected solder portion to be unacceptable when the first means determines the image of the inspected solder portion to be similar to one of the images of typical solder portions each corresponding to an unacceptable solder portion;

third means connected to the first means for determining whether the inspected solder portion is acceptable or unacceptable when the first means determines the image of the inspected solder portion to be not similar to one of the images of the typical solder portions; and fourth means connected to the first means and the third means for enabling the first means to include the image of the inspected solder portion as an image of an additional typical solder portion in said images of typical solder portions used by the first means, for adding the image of the inspected solder portion to said images of typical solder portions as an image of a new typical solder portion, and for providing a correspondence relation between the new typical solder portion and one of an acceptable solder portion and an unacceptable solder portion in response to a result of the determination by the third means in cases where the first means determines the image of the inspected solder portion to be not similar to one of the images of the typical solder portions.

14. The apparatus of claim 13, wherein the first means and the fourth means comprise a CPU forming a neural network model, and said fourth means enables the neural network of the first means to learn the image of the inspected solder portion.

15. A method of inspecting a solder portion, comprising the steps of:

first deciding whether or non an image of a solder portion being inspected is similar to one of images of typical solder portions to decide whether the inspected solder portion is acceptable or unacceptable;

second deciding whether the inspected solder portion is acceptable or unacceptable to supplement the decision by the first deciding step when image of the inspected solder portion is decided to be not similar to one of the images of the typical solder portions by the first deciding step; and including the image of the inspected solder portion and adding the learned image of the inspected solder portion to said images of typical solder portions as an image of a new typical solder portion in the decision by the first deciding step when the image of the inspected solder portion is decided to be not similar to one of the images of the typical solder portions by the first deciding step.

16. A method of inspecting a solder portion, comprising the steps of:

first determining whether or not an image of a solder portion being inspected is similar to one of images of typical solder portions to each corresponding to either an acceptable solder portion or an unacceptable solder portion;

first deciding the inspected solder portion to be acceptable when the first determining step determines the image of the inspected solder portion to be similar to one of images of typical solder portions each corresponding to an acceptable solder portion, and deciding the inspected solder portion to be unacceptable when the first determining step determines the image of the inspected solder portion to be similar to one of images of typical solder portions each corresponding to an unacceptable solder portion;

second deciding whether the inspected solder portion is acceptable or unacceptable when the first determining step determines image of the inspected solder portion to be not similar to one of the images of the typical solder portions; and including the image of the inspected solder portion, adding the included image of the inspected solder portion to said images of typical solder portions as an image of a new typical solder portion, and providing a correspondence relation between the new typical solder portion and one of an acceptable solder portion and an unacceptable solder portion in response to a result of the determination by the second determining step in cases where the first determining step determines the image of the inspected solder portion to be not similar to one of the images of the typical solder portions.

* * * * *